United States Patent
Goddard et al.

(10) Patent No.: US 11,612,716 B2
(45) Date of Patent: Mar. 28, 2023

(54) STERILIZABLE FIDUCIAL BEACON STRAND FOR RF TARGET TRACKING

(71) Applicant: MONTEFIORE MEDICAL CENTER, Bronx, NY (US)

(72) Inventors: Lee Goddard, Harrison, NY (US); Madhur Garg, Ardsley, NY (US); Wolfgang Tomé, Ardsley, NY (US); Carlo Greco, Estoril (PT)

(73) Assignee: MONTEFIORE MEDICAL CENTER, Bronx, NY (US)

( * ) Notice: Subject to any disclaimer, the term of this patent is extended or adjusted under 35 U.S.C. 154(b) by 749 days.

(21) Appl. No.: 16/482,724

(22) PCT Filed: Jan. 22, 2018

(86) PCT No.: PCT/US2018/014639
§ 371 (c)(1),
(2) Date: Aug. 1, 2019

(87) PCT Pub. No.: WO2018/144258
PCT Pub. Date: Aug. 9, 2018

(65) Prior Publication Data
US 2021/0283370 A1 Sep. 16, 2021

Related U.S. Application Data

(60) Provisional application No. 62/453,050, filed on Feb. 1, 2017.

(51) Int. Cl.
*A61N 5/10* (2006.01)
*A61M 25/00* (2006.01)

(52) U.S. Cl.
CPC ....... *A61M 25/0041* (2013.01); *A61N 5/1042* (2013.01); *A61N 5/1049* (2013.01);
(Continued)

(58) Field of Classification Search
CPC ............ A61B 1/00002; A61B 1/00004; A61B 1/00009; A61B 1/000094; A61B 1/000095; A61B 1/00059; A61B 1/00064; A61B 1/00071; A61B 1/00096; A61B 1/00112; A61B 1/00114; A61B 1/00119; A61B 1/00131; A61B 1/00137; A61B 1/0014;
(Continued)

(56) References Cited

U.S. PATENT DOCUMENTS 6,261,247 B1 7/2001 Ishikawa et al.
8,939,153 B1 1/2015 Reicher et al.
(Continued)

FOREIGN PATENT DOCUMENTS

WO 2015150527 A1 10/2015

OTHER PUBLICATIONS

PCT International Search Report and Written Opinion dated May 17, 2018 for PCT International Patent Application No. PCT/US2018/014639.

*Primary Examiner* — Irakli Kiknadze
(74) *Attorney, Agent, or Firm* — Perkins Coie LLP

(57) ABSTRACT

A sterilizable device comprising electromagnetic transponders separated from one another by a flexible spacer material enclosed within radiofrequency-transparent sterilizable tubing for target tracking during prostate treatments, and method of use thereof.

18 Claims, 3 Drawing Sheets

(52) U.S. Cl.
CPC ............... *A61M 2205/3317* (2013.01); *A61M 2205/3553* (2013.01); *A61M 2210/166* (2013.01); *A61N 2005/1051* (2013.01); *A61N 2005/1055* (2013.01); *A61N 2005/1061* (2013.01)

(58) Field of Classification Search
CPC ............ A61B 1/00142; A61B 1/00144; A61B 1/00158; A61B 1/005; A61B 1/0058; A61B 1/018; A61B 1/04; A61B 1/043; A61B 1/044; A61B 1/31; A61B 90/39; A61B 6/04; A61B 6/0492; A61B 6/4423; A61B 6/547; A61B 2017/00292; A61B 2017/00296; A61B 2017/00336; A61B 2017/00902; A61B 2017/0092; A61B 2090/3904; A61B 2090/3912; A61B 2090/392; A61B 2090/3937; A61B 2090/3945; A61B 2090/3954; A61B 2090/3958; A61B 2090/3966; A61B 2090/3983; A61B 2090/3975; A61B 90/36; A61B 17/3403; A61B 90/98; A61B 17/32; A61B 18/14; A61B 2090/395; A61B 18/02; A61B 2090/3933; A61B 2090/3987; A61B 2017/00053; A61B 18/042; A61B 2017/00022; A61B 2017/00026; A61B 2017/00411; A61B 17/22004; A61B 2018/00547; A61B 2018/00559; A61N 5/10; A61N 5/1007; A61N 5/1037; A61N 5/1048; A61N 5/1049; A61N 5/1064; A61N 2005/1051; A61N 2005/1061; A61N 2005/1072; A61N 2005/1076; A61N 5/1042; A61N 5/1071; A61N 2005/1055; A61N 1/05; A61N 2005/1097; A61M 25/0021; A61M 25/0041; A61M 2202/0007; A61M 2202/0014; A61M 2202/0021; A61M 2205/051; A61M 2205/11; A61M 2205/3317; A61M 2205/3561; A61M 2210/16; A61M 2210/166; A61M 2205/3553; A61M 25/04; A61M 25/0108
USPC ........................................ 378/62–65; 604/514
See application file for complete search history.

(56) References Cited

U.S. PATENT DOCUMENTS

| | | |
|---|---|---|
| 2004/0204645 A1 | 10/2004 | Saadat et al. |
| 2010/0168561 A1* | 7/2010 | Anderson ............. A61B 90/36 600/424 |
| 2013/0217999 A1 | 8/2013 | Burnside et al. |
| 2016/0128797 A1 | 5/2016 | Burbank et al. |
| 2017/0113066 A1* | 4/2017 | Greco ................. A61N 5/1067 |

* cited by examiner

# STERILIZABLE FIDUCIAL BEACON STRAND FOR RF TARGET TRACKING

CROSS-REFERENCE TO RELATED APPLICATIONS

This application is a U.S. national stage entry under 35 U.S.C. § 371 of PCT International Patent Application No. PCT/US2018/014639, filed Jan. 22, 2018, which claims the benefit of U.S. Provisional Patent Application No. 62/453,050, filed Feb. 1, 2017, the contents of each of which are incorporated herein by reference into the subject application.

BACKGROUND OF THE INVENTION

Throughout this application various publications, patents, patent application publications and books are referred to. Full citations for the publications may be found at the end of the specification. The disclosures of the publications, patents, patent application publications and books are hereby incorporated by reference in their entirety into the subject application to more fully describe the art to which the subject invention pertains.

The present invention addresses the need of providing improved techniques for active transponders use in courses of therapy using MRI assessment between multiple radiofrequency energy treatments.

SUMMARY OF THE INVENTION

A device is provided comprising (i) at least three electromagnetic transponders separated from one another by a flexible spacer material, all of which are (ii) enclosed within radiofrequency-transparent sterilizable tubing.

A method of treating a prostate cancer in a subject comprising:
inserting the device as described herein into a prostate of the subject;
monitoring by cone beam CT imaging the location of the prostate within the subject;
administering an amount of external beam radiation therapy (EBRT) to the prostate of the subject;
monitoring movement of the prostate during administration of EBRT by monitoring the location of the at least three electromagnetic beacon transponders by exciting them with radiofrequency energy and collecting the signal therefrom.

A method of treating a prostate cancer in a subject comprising:
inserting the device as described into a prostate of the subject;
monitoring by CT imaging the location of the prostate within the subject;
administering an amount of external beam radiation therapy (EBRT) to the prostate of the subject;
monitoring movement of the prostate during administration of EBRT by monitoring the location of the at least three electromagnetic beacon transponders by exciting them with radiofrequency energy and collecting the signal therefrom;
removing the device from the subject;
subjecting the prostate of the subject to a magnetic resonance imaging (MRI) scan to analyze the effect of the EBRT;
sterilizing the device and re-inserting it into the prostate of the subject;
monitoring by CT imaging the location of the prostate within the subject;
administering an amount of external beam radiation therapy (EBRT) to the prostate of the subject;
monitoring movement of the prostate during administration of EBRT by monitoring the location of the at least three electromagnetic beacon transponders by exciting them with radiofrequency energy and collecting the signal therefrom.

Also provided is a method of manufacturing a device comprising:
(i) assembling at least three electromagnetic transponders in a line and separating a middle electromagnetic transponder from the remaining electromagnetic transponders by an amount of a flexible spacer material;
(ii) enclosing the product of step (i) within a first layer polyethylene terephthalate heat shrink tubing;
(iii) enclosing the product of step (ii) within a second layer polyethylene terephthalate heat shrink tubing.

Additional objects of the invention will be apparent from the description which follows.

DETAILED DESCRIPTION OF THE INVENTION

Figure 1:
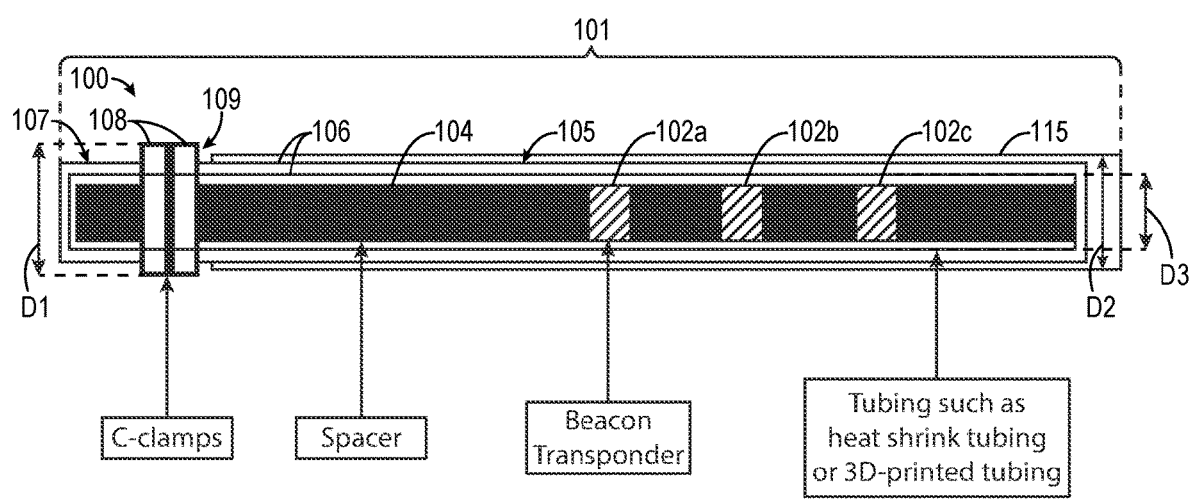
FIG. 1: Schematic of a device.
Figure 1A:
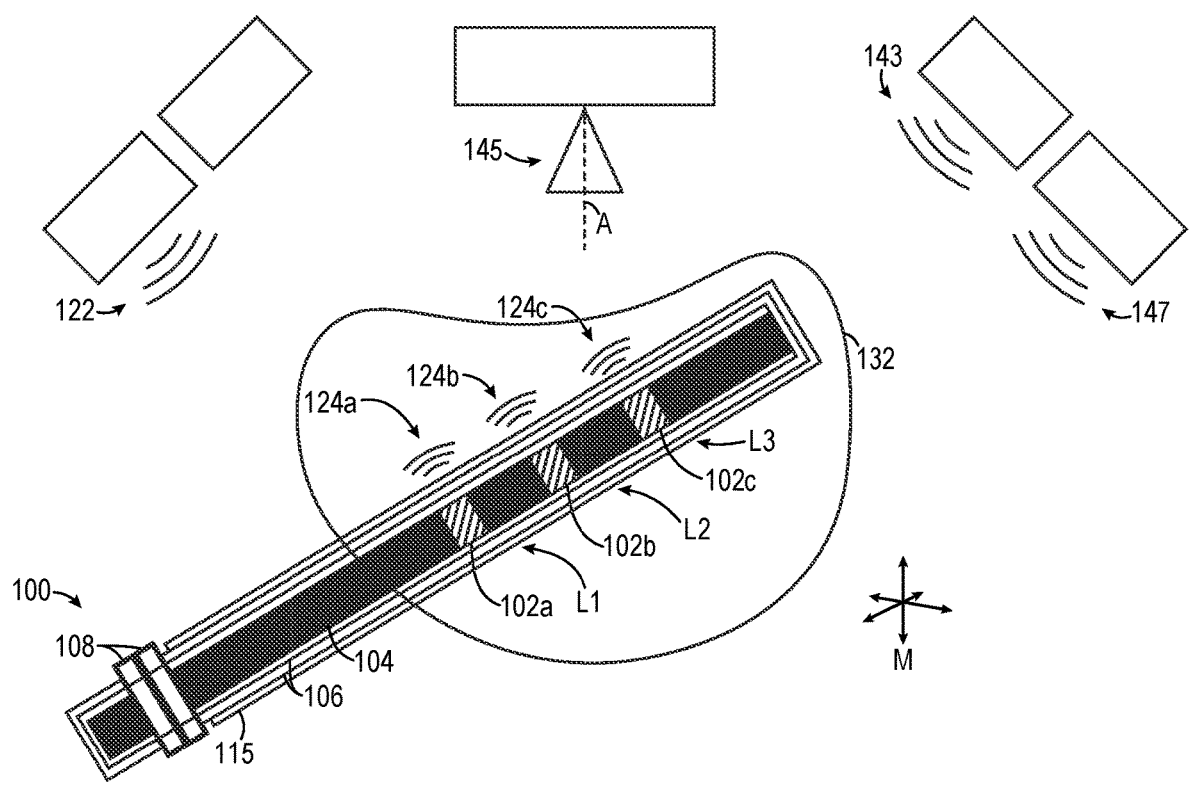
FIG. 1A: Schematic of the device of FIG. 1, a prostate, and associated devices.
Figure 2:
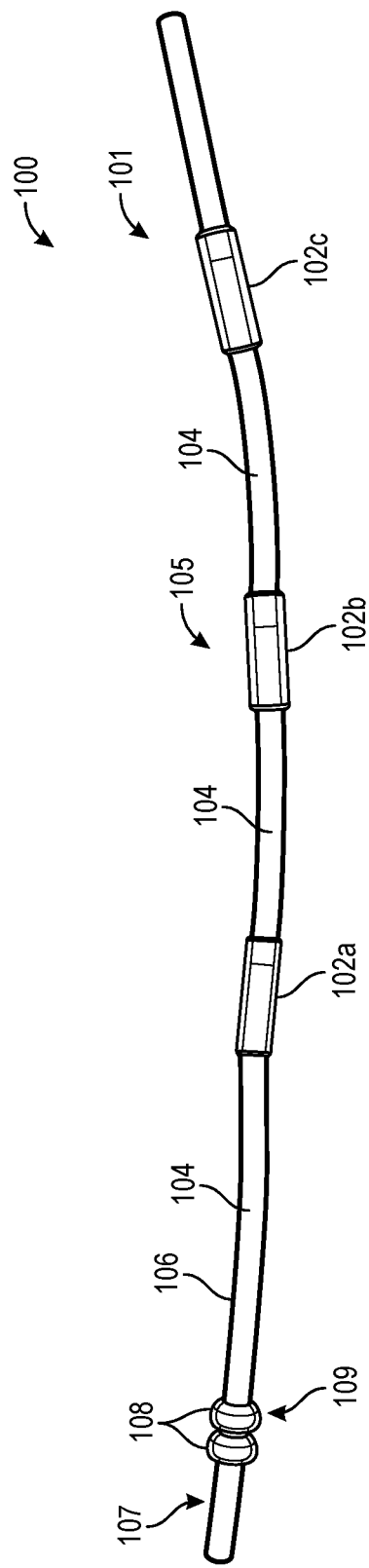
FIG. 2: Photo of exemplary product showing sterling silver C-clamps on left hand portion and three transponders within the strand.

A device 100 is provided comprising (i) at least three electromagnetic transponders 102a-102c separated from one another by a flexible spacer material 104, all of which are (ii) enclosed within radiofrequency-transparent sterilizable tubing 106.

In an embodiment, the device 100 further comprises one or more silver metal clamps 108 clamped around a portion of the device 100. In an embodiment, the one or more silver metal c-type clamps 108 are crimped around a portion of the strand 101 to provide a stop 109 having increased diameter D1 relative to the remainder of the strand 101.

In an embodiment, the device 100 is in the form of a strand 101.

In an embodiment, the device 100 is in inserted into a Foley catheter 115, wherein the one or more clamps 108 are wider in diameter D1 than the internal diameter D2 of the Foley catheter 115. In an embodiment, the clamps 108 are silver metal c-type clamps.

In an embodiment, the one or more clamps 108 prevent insertion of an unclamped portion 107 of the device 100 into a Foley catheter 115 when a remaining portion 105 of the device 100 is inserted into the Foley catheter 115. In an embodiment, the clamps 108 are silver metal c-type clamps.

In an embodiment, the size of the Foley catheter 115 is in a range from 10F to 28F.

In an embodiment, the electromagnetic transponders 102a-102c are passive electromagnetic oscillators, ("transponders"), that emit a unique electromagnetic signal 124a-124c when excited using an external transmitted electromagnetic signal 122. In an embodiment, the transponders 102a-102c are low activity Ir-192 seeds.

In an embodiment, the transponders 102a-102c wirelessly emit an electromagnetic signal 124a-124c when subjected to an artificially induced electromagnetic field 122.

In an embodiment, the sterilizable radiofrequency-transparent tubing 106 is polyethylene terephthalate heat shrink tubing. In an embodiment, the sterilizable radiofrequency-transparent tubing 106 is a plastic tubing. In an embodiment, the sterilizable radiofrequency-transparent tubing 106 is 3D-printed tubing.

A method of treating a prostate cancer in a subject comprising:
inserting the device 100 as described herein into a prostate 132 of the subject;
monitoring by cone beam CT imaging 143 the location of the prostate 132 within the subject;
administering an amount of external beam radiation therapy (EBRT) 145 to the prostate 132 of the subject;
monitoring movement M of the prostate 132 during administration of EBRT 145 by monitoring the location L1, L2, L3 of the at least three electromagnetic beacon transponders 102a-102c by exciting them with radiofrequency energy 122 and collecting the signal 124a-124c therefrom.

A method of treating a prostate cancer in a subject comprising:
inserting the device 100 as described into a prostate 132 of the subject;
monitoring by CT imaging 143 the location of the prostate 132 within the subject;
administering an amount of external beam radiation therapy (EBRT) 145 to the prostate 132 of the subject;
monitoring movement M of the prostate 132 during administration of EBRT 145 by monitoring the location L1, L2, L3 of the at least three electromagnetic beacon transponders 102a-102c by exciting them with radiofrequency energy 122 and collecting the signal 124a-124c therefrom;
removing the device 100 from the subject;
subjecting the prostate 132 of the subject to a magnetic resonance imaging (MRI) scan 147 to analyze the effect of the EBRT 145;
sterilizing the device 100 and re-inserting it into the prostate 132 of the subject;
monitoring by CT imaging 143 the location of the prostate 132 within the subject;
administering an amount of external beam radiation therapy (EBRT) 145 to the prostate 132 of the subject;
monitoring movement M of the prostate 132 during administration of EBRT 145 by monitoring the location L1, L2, L3 of the at least three electromagnetic beacon transponders 102a-102c by exciting them with radiofrequency energy 122 and collecting the signal 124a-124c therefrom.

In an embodiment, the methods further comprise moving the subject in whom the prostate 132 has been monitored as having moved, so as to position the subject's prostate 132 in the line of the therapeutic axis A of the EBRT 145.

In an embodiment, the EBRT 145 is stereotactic body radiation therapy.

In an embodiment, the method further comprises removing the device 100 from the subject after administering the amount of external beam radiation therapy (EBRT) 145 and sterilizing the device 100 for re-use.

In an embodiment, the electromagnetic transponders 102a-102c are each less than 1 cm in length and less than 2 mm in diameter.

In an embodiment, if the monitoring by CT 143 shows a movement M of 1 mm or more, then the EBRT 145 is re-positioned to ensure it is targeted at the prostate 132 of the subject so moved.

Also provided is a method of manufacturing a device 100 comprising:
assembling at least three electromagnetic transponders 102a-102c in a line and separating a middle electromagnetic transponder 102b from the remaining electromagnetic transponders 102a and 102c by an amount of a flexible spacer material 104;
enclosing the product of step (i) within a first layer polyethylene terephthalate heat shrink tubing 106;
enclosing the product of step (ii) within a second layer polyethylene terephthalate heat shrink tubing 106,
so as to form the device 100.

In an embodiment, the method further comprises clamping one or more silver metal clamps 108 around a portion of the device 100.

In an embodiment, the device 100 is manufactured in the form of a strand 101.

In an embodiment, the electromagnetic transponder 102 is configured to wirelessly transmit a location signal 124 in response to wirelessly transmitted non-ionizing excitation energy 122. In an embodiment, the electromagnetic transponder 102 is configured to wirelessly transmit a location signal 124 in response to wirelessly transmitted radiofrequency excitation energy 122.

In an embodiment, each transponder 102 emits a signal 124 in response to non-ionizing excitation energy 122 at a unique frequency specific to that transponder 102.

In an embodiment, the electromagnetic transponder 102 contains an electrical circuit contained within a glass vial.

The subject of the methods may be any subject. Preferably, the subject is a mammal. More preferably, the subject is a human.

As used herein "and/or", for example as in option A and/or option B, means the following embodiments: (i) option A, (ii) option B, and (iii) the option A plus B, and any subset of such options, including only one option.

All combinations of the various elements described herein are within the scope of the invention unless otherwise indicated herein or otherwise clearly contradicted by context.

Where a numerical range is provided herein, it is understood that all numerical subsets of that range, and all the numerical values to one decimal place, are provided as part of the invention. Thus, for example, an ablation catheter which is 10F-28F in size includes the subset of ablation catheters which are 11F, 12F, 13F, etc. in size as well as the range of ablation catheters which are 15F-20F, 18F-28F, and so forth.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Examples

When delivering External Beam Radiation Therapy (EBRT) for the treatment of prostate cancer, beacon transponders (e.g., Calypso™ by Varian Medical Systems) can be implanted within the prostate to allow for target localization and tracking during the course of the treatment. Typically three transponders are implanted into the prostate before CT imaging and treatment begin. These transponders remain within the patient after treatment is completed and cannot be removed without surgery.

High dose per fraction EBRT, known as Stereotactic Body Radiation Therapy (SBRT) for the treatment of prostate cancer is becoming increasingly common as recent studies have shown similar/improved local control compared to conventional treatment regimens. SBRT reduces the number of treatments from 43 to 5 or fewer, making it much easier for the patient. Beacon transponders are required when delivering SBRT to allow for precise target localization during radiation delivery. The position of the prostate can change within the course of a single treatment due to organ motion; the calypso system allows for the motion of the prostate to be tracked during treatment delivery and can halt the treatment if large shifts are detected. Due to the higher dose being delivered precise target and organ at risk delineation is essential. For this reason, an MRI is an essential tool both for pre-treatment imaging and also as a follow up in case of disease recurrence.

Beacon transponders are essentially radio-frequency transponders and thus cause large artifacts in an MRI study. Each transponder creates a sphere approximately 2 cm in radius where there is no measured MRI signal. This effectively prevents MRI studies of the prostate.

Previous work (Champalimaud Centre for the Unknown, Lisbon, Portugal) has placed Calypso transponders directly into the central lumen of a Foley catheter. This catheter is then inserted into the patient's urethra prior to treatment and removed after treatment. The catheter is sterilized using gamma sterilization between treatments. In some countries, however, including the U.S., Foley catheters are classed as single use devices. There is no FDA approved method of sterilization of such.

Herein an improved method and device for tracking and imaging studies using transponders 102 in a single product 100 is provided which is removable, sterilizable and reusable.

In an embodiment, the beacon transponder strand 101 consists of three beacon transponders 102a-102c (e.g., of the Calypso type) and a flexible beading spacer material 104 (e.g., a thermoplastic elastomers comprising polyamide and polyether backbone, e.g., Pebax™ by Vention Medical). This is enclosed in a medical grade polyethylene terephthalate heat shrink tubing 106 (e.g., Vention Medical). In an embodiment, in the manufacture of the beacon transponder strand 101, the strand 101 containing the transponders 102a-102c, spacer material 104, and covered in heat shrink tubing 106 is placed in a water bath (e.g., 275° F., 15 minutes) causing the outer tubing 106 to shrink to the diameter D3 of the transponders 102a-102c and spacer material 104. The strand 101 is then placed in a second layer of tubing 106 and heated once more for added strength. Finally, it is preferable that one or more clamps 108, such as sterling silver c type clamps, are crimped to the strand 101 to prevent the device 100 being inserted into a Foley catheter 115 further than desired. The final device 100 can be re-sterilized multiplied times, e.g., using a technique such as low temperature ethylene oxide (ETO) or low-temperature, hydrogen peroxide gas plasma (e.g., Sterrad™, Advanced Sterilization Products).

What is claimed is:

1. A device in the form of a strand having a first portion insertable into a catheter, the device comprising:
at least three electromagnetic transponders separated from one another by a flexible spacer material, all of which are enclosed within radiofrequency-transparent sterilizable tubing; and
one or more clamps different from the flexible spacer material and the radiofrequency-transparent sterilizable tubing, and crimped around a second portion of the strand to provide a stop having an increased diameter relative to an external diameter of the first portion of the strand, wherein the one or more clamps are wider in a diameter than an internal diameter of the catheter.

2. The device of claim 1, wherein the one or more clamps include one or more silver metal c-type clamps.

3. The device of claim 1, wherein the catheter includes a Foley catheter.

4. The device of claim 1, wherein the one or more clamps prevent insertion of an unclamped third portion of the device into catheter at least when the first portion of the device is inserted into the catheter.

5. The device of claim 1, wherein a size of the catheter is in a range from 10-F to 28-F.

6. The device of claim 1, wherein the electromagnetic transponders are configured to emit an electromagnetic signal when externally excited.

7. The device of claim 1, wherein the electromagnetic transponders are configured to wirelessly emit an electromagnetic signal when subjected to an artificially induced electromagnetic field.

8. The device of claim 1, wherein the sterilizable radiofrequency-transparent tubing is polyethylene terephthalate heat shrink tubing.

9. The device of claim 1, wherein the sterilizable radiofrequency-transparent tubing is 3D-printed tubing.

10. A method of treating a prostate cancer in a subject comprising:
inserting the device of claim 1 into a prostate of the subject;
monitoring by cone beam CT imaging a location of the prostate within the subject;
administering an amount of external beam radiation therapy (EBRT) to the prostate of the subject;
monitoring movement of the prostate during administration of the EBRT by monitoring first locations of the at least three electromagnetic transponders by exciting them with radiofrequency energy and collecting corresponding signals therefrom.

11. The method of claim 10, further comprising re-positioning the EBRT to target the EBRT at the prostate when the monitoring of the first location or the second location by CT shows a movement of the prostate of 1 mm or more.

12. A method of treating a prostate cancer in a subject comprising:
inserting the device of claim 1 into a prostate of the subject;
monitoring by CT imaging a first location of the prostate within the subject;
administering a first amount of external beam radiation therapy (EBRT) to the prostate of the subject;
monitoring first movement of the prostate during administration of the first amount of the EBRT by monitoring first locations of the at least three electromagnetic transponders by exciting them with first radiofrequency energy and collecting first corresponding signals therefrom;
removing the device from the subject;
subjecting the prostate of the subject to a magnetic resonance imaging (MRI) scan to analyze an effect of the EBRT;
sterilizing the device and re-inserting it into the prostate of the subject;
monitoring by CT imaging a second location of the prostate within the subject;
administering a second amount of the EBRT to the prostate of the subject;

monitoring second movement of the prostate during administration of the second amount of the EBRT by monitoring second locations of the at least three electromagnetic transponders by exciting them with second radiofrequency energy and collecting second corresponding signals therefrom.

13. The method of claim 12, wherein the EBRT is stereotactic body radiation therapy.

14. The method of claim 12, further comprising (a) removing the device from the subject after administering the second amount of the EBRT, and (b) re-sterilizing the device for re-use.

15. The device of claim 1, wherein each of the at least three electromagnetic transponders is less than 1 cm in length and less than 2 mm in diameter.

16. A device, comprising: at least three electromagnetic transponders separated from one another by flexible spacer material, all of which are enclosed within radiofrequency-transparent sterilizable tubing; and one or more clamps different from the flexible spacer material and the radiofrequency-transparent sterilizable tubing, and clamped around a portion of the device, wherein the one or more clamps include one or more silver metal clamps.

17. The device of claim 16, wherein the one or more clamps include one or more c-type clamps.

18. The device of claim 16, wherein the portion of the device is a first portion of the device is a first portion of the device; the device includes a second portion insertable into a lumen of a catheter; the one or more clamps are clamped around the first portion of the device such that at least one clamp of the one or more clamps forms a stop having an increased diameter relative to (a) a diameter of the lumen of the catheter and (b) an external diameter of the second portion of the device; and the stop prevents insertion of the device into the lumen of the catheter beyond the second portion of the device.

* * * * *

UNITED STATES PATENT AND TRADEMARK OFFICE
CERTIFICATE OF CORRECTION

PATENT NO. : 11,612,716 B2  
APPLICATION NO. : 16/482724  
DATED : March 28, 2023  
INVENTOR(S) : Lee Goddard et al.

Page 1 of 1

It is certified that error appears in the above-identified patent and that said Letters Patent is hereby corrected as shown below:

In the Claims

• In Column 8, Lines 7-8, in Claim 18, delete "portion of the device is a first portion of the device is a first" and insert -- portion of the device is a first --, therefor.

Signed and Sealed this  
Fifth Day of March, 2024

Katherine Kelly Vidal  
*Director of the United States Patent and Trademark Office*